United States Patent [19]

Cramm et al.

[11] Patent Number: 5,677,453

[45] Date of Patent: Oct. 14, 1997

[54] PROCESS FOR THE PREPARATION OF 4,6-DICHLOROPYRIMIDINES

[75] Inventors: Günther Cramm; Volker Käss, both of Leverkusen; Guido Steffan, Odenthal, all of Germany

[73] Assignee: Bayer Aktiengesellschaft, Leverkusen, Germany

[21] Appl. No.: 699,812

[22] Filed: Aug. 19, 1996

[30] Foreign Application Priority Data

Aug. 25, 1995 [DE] Germany .................. 195 31 299.6

[51] Int. Cl.⁶ .............................................. C07D 239/30
[52] U.S. Cl. ............................................................ 544/334
[58] Field of Search ................................................ 544/334

[56] References Cited

FOREIGN PATENT DOCUMENTS

| | | |
|---|---|---|
| 0 251 246 A1 | 1/1988 | European Pat. Off. . |
| 0 697 406 A1 | 2/1996 | European Pat. Off. . |
| WO 95/29166 | 11/1995 | WIPO . |
| WO 96/23776 | 8/1996 | WIPO . |

OTHER PUBLICATIONS

Hennart et al., Contribution a la synthesis de la dichloro–4–6 pyrimidine—Societe Chimique de France No. 140, (1959) pp. 741–742.

R. Hull, A New Sythesis of 4:6–dihydroxypyrimidines—J. Chem. Soc. (1951) p. 2214.

Contribution à la synthèse de la dichloro–4–6 pyrimidine, Hennart et al., Bull. de la Soc. Chim. France, (1959) pp. 741–742.

Experiments on the Synthesis of Purine Nucleosides. Part IV...., Kenner et al., J. Chem. Soc. (1943), pp. 574–575.

A New Synthesis of 4:6–Dihydroxpyrimidines, Hull, J. Chem. Soc. (1951), p. 2214.

Synthesis of 4–(p–Aminobenzenesulfonamido)–6–Methoxypyrimidine, Zasosov et al., Translated from Khimiko–Farmatsevticheskii Zhurnal, vol. 8, No. 12, pp. 28–31, Dec., 1974. Original article submitted Dec. 6, 1973.

*Primary Examiner*—John M. Ford
*Attorney, Agent, or Firm*—Sprung Horn Kramer & Woods

[57] ABSTRACT

4,6-Dichloropyrimidines are obtained by the reaction of 4,6-dihydroxypyrimidines with excess phosphoryl chloride in a particularly advantageous manner when no base is added, during and/or after the reaction 0.75 to 1.5 mol of phosphorus trichloride and 0.7 to 1.3 mol of chlorine are added per equivalent of exchanged hydroxyl groups so that an excess of phosphorus trichloride with respect to chlorine is always present, and finally phosphorus trichloride and phosphoryl chloride are separated off. This process can be carried out in a particularly simple manner and also continuously.

10 Claims, No Drawings

PROCESS FOR THE PREPARATION OF 4,6-DICHLOROPYRIMIDINES

The present invention relates to an improved process for the preparation of 4,6-dichloropyrimidines from 4,6-dihydroxypyrimidines.

4,6-Dichloropyrimidines are intermediates, for example in the preparation of plant protection agents and dyes.

In known processes for the preparation of 4,6-dichloropyrimidines, 4,6-dihydroxypyrimidines are admixed with phosphoryl chloride and a base such as dimethylaniline or pyridine (see J. Chem. Soc. 1943, 574; J. Chem. Soc. 1951, 2214;Bull. Soc. Chim. France 1959, 741 and Khim.-Pharm. Zhurnal 8(12), 28 (1974)-English translation p. 741).

For the work-up, the excess phosphoryl chloride is first drawn off and the residue is either added to ice and the product obtained by extraction and distillation or is subjected to a sublimation process by which the product is obtained as sublimate. In this process, it is disadvantageous that the bases are used in large quantities, but can only be recovered and reused at considerable cost. Finally, an aqueous work-up is very costly because of the disposal of the waste water formed and the handling of extractants. A work-up by sublimation is also very costly on the industrial scale, for example with respect to the apparatus to be used and the occupational hygiene conditions for removal of the product from the sublimer.

Some attempts to improve the known processes by the use of smaller amounts of bases failed because the yield of 4,6-dichloropyrimidines is greatly reduced and the formation of high boilers and resins greatly increases (see Example 5).

A process has now been found for the preparation of 4,6-dichloropyrimidines by the reaction of 4,6-dihydroxypyrimidines with excess phosphoryl chloride, characterized in that no base is added, after the reaction from 0.7 to 1.3 mol of chlorine is added per equivalent of exchanged hydroxyl group in the presence of phosphorus trichloride so that an excess of phosphorus trichloride with respect to chlorine is always present, and finally the phosphorus trichloride and phosphoryl oxychloride are separated off.

In the process of the invention, for example 4,6-dihydroxypyrimidine or 4,6-dihydroxypyrimidines substituted in position 2 and/or position 5 with, for example, $C_1$–$C_{10}$-alkyl and/or $C_6$–$C_{10}$-aryl groups can be used. The alkyl and aryl groups can in turn if desired contain, for example, halogen, nitro and/or $C_1$–$C_6$-alkoxy as substituents. Independently of a substitution in position 2, 5-halogen-, for example, 5-chlorine-substituted 4,6-dihydroxypyrimidines can be used. Preferably, 4,6-dihydroxypyrimidine is used. Where 4,6-dihydroxypyrimidines or 4,6-dihydroxypyrimidines are referred to below, the substituted types shall be regarded as included.

For each mole of 4,6-dihydroxypyrimidine used, for example 2.5 to 12 mol of phosphoryl chloride can be used. This amount is preferably from 3.5 to 5 mol.

For the reaction of 4,6-dihydroxypyrimidines with phosphoryl chloride, temperatures for example in the range 60° to 110° C. are suitable. Temperatures from 80 to 100° C. are preferred. It is possible to proceed so that, for example, the phosphoryl chloride is added first and the 4,6-dihydroxypyrimidine is metered into it. Other working methods are also possible.

Preferably after the 4,6-dihydroxypyrimidine used has dissolved in the phosphoryl chloride, the reaction mixture is admixed with phosphorus trichloride and the amount of chlorine given above so that always an excess of phosphorus trichloride with respect to chlorine is present in the reaction mixture. The excess is preferably determined so that from 0.3 to 5% by weight, preferably from 1 to 3% by weight of free phosphorus trichloride is always present. It is possible to proceed so that phosphorus trichloride and chlorine are metered in at a uniform rate, with a brief prior addition of phosphorus trichloride.

Per equivalent of exchanged hydroxyl groups, for example from 0.75 to 1.5 mol of phosphorus trichloride can be added, taking care that an excess thereof with respect to chlorine is always present.

The addition of phosphorus trichloride and chlorine can be carried out, for example, at from 60° to 110° C. Temperatures of from 80° to 100° C. are preferred. When the addition of phosphorus trichloride and chlorine is complete, it can be advantageous, especially in batchwise operation, to after-stir the mixture at from 60° to 110° C. for some time, for example for 10 minutes to 3 hours.

After completion of the reaction with phosphorus trichloride and chlorine, the reaction mixture can be worked up, for example by distillation.

Because of the dilution effect of the phosphoryl chloride present in the batch, it can be advantageous to use only a part of the reaction mixture for the work-up, and to admix the remainder, if desired after addition of phosphoryl chloride, so that the proportion of this in the reaction mixture does not fall below a predetermined value, with fresh 4,6-dihydroxypyrimidine and, after complete reaction of the latter, to react again with the corresponding amount of phosphorus trichloride and chlorine. This procedure can be repeated as often as desired.

The addition of phosphorus trichloride can also be carried out before or simultaneously with the addition of the 4,6-dihydroxypyrimidine. It can thus be advantageous for practical operation to add the 4,6-dihydroxypyrimidines as a suspension in phosphorus trichloride. In this case, the addition of phosphorus trichloride before the addition of chlorine can be omitted.

It has been found to be particularly favourable to carry out this reaction sequence and the subsequent distillation separation continuously.

The removal of phosphoryl trichloride and phosphoryl chloride can, according to whether the process of the invention is carried out batchwise, semicontinuously, or continuously, be carried out in various ways.

In batchwise operation, for example, the whole of the reaction mixture can be subjected to a distillation, preferably at reduced pressure, and the phosphorus trichloride and phosphorus oxychloride can be separated off in succession.

In semicontinuous operation, the procedure can be, for example, first adding to a completely reacted reaction mixture more 4,6-dihydroxypyrimidine followed by phosphorus trichloride and chlorine in the manner described above, in the amounts described above, and at the temperatures described above, and allowing the reaction to proceed. This further addition can, depending on the size of the reaction vessel used, be repeated a number of times, for example up to 20 times. Part of the reaction mixture so produced can then be removed, preferably over a range of ±20% by weight of the amount of the increase in weight since the first addition of 4,6-dihydroxypyrimidine. Phosphoryl chloride, then 4,6-dihydroxypyrimidine, and then phosphorus trichloride and chlorine can then be added again to the residue as described above, and, after the reaction has subsided, a part of the reaction mixture can be removed, preferably with a range of from ±20% by weight of the amount that corresponds to the increase in weight since the addition of 4,6-dihydroxypyrimidine. This cycle can be repeated as often as desired, for example up to 50 times.

The portions of the reaction mixture separated off in this procedure can be subjected, for example, to a distillation, preferably under reduced pressure, and the phosphorus trichloride and phosphorus oxychloride can be separated off in succession. These two products can be recycled to the process. Excess phosphoryl chloride can be further used in any any desired manner. This also applies to phosphorus trichloride and phosphoryl chloride separated off using any other working methods.

In a continuous operating method, for example the completely reacted reaction mixture of a batch reaction can be placed in a reaction vessel which ensures that the reaction proceeds with minimal backmixing, if any, for example a multiple chamber reactor, and 4,6-dihydroxypyrimidine is there continuously added, for example suspended in phosphorus trichloride, and phosphoryl chloride, while adhering to the conditions described above. The reactor, in the case of a multiple chamber reactor, on having from 4 to 12 chambers, for example, is maintained at the reaction temperature, and chlorine is continuously introduced in the manner described above and in the amounts described above at some distance from the other addition points. The mixture leaving the reactor can be collected in a buffer tank from which it can be fed back into the reaction, and the remainder can be fed to a distillation work-up stage. The distillation work-up can be carried out at reduced pressure, and, for example, can be divided into three parts, such that in the first distillation apparatus, for example a column, excess phosphorus trichloride can be removed, in a second distillation apparatus, for example a column, phosphoryl chloride can be removed, and, in a third distillation apparatus, for example a thin film evaporator, the 4,6-dichloropyrimidine produced can be separated off.

In the batchwise and the semicontinuous operations, after removal of phosphorus trichloride and phosphoryl chloride, the 4,6-dichloropyrimidines produced can be isolated from the remaining residues by distillation, preferably under reduced pressure.

In the distillation removal of the 4,6-dichloropyrimidines produced, it is advantageous to use a driving liquid and/or a flow agent for the distillation residue. Suitable materials for this include, for example, high boiling, thermally stable substances, for example polywaxes, for example on the basis of oligo- or polyethylene glycols, ditolyl ether, polychlorobenzenes and polychlorotoluenes and dialkyl phthalates.

The process of the invention provides for the preparation of 4,6-dichloropyrimidines in yields of over 80%, frequently over 85%, of theory. This is particularly surprising because no base is used, which had hitherto been considered to be essential. As a result, handling of the base and its separation from the reaction mixture is no longer necessary, which significantly simplifies the reaction process and also makes continuous operation possible.

It is also possible to operate the process of the invention in such a way that yields of 4,6-dichloropyrimidines in excess of 95% of theory are obtained. This can be achieved for example in the case of continuous operation by reducing the amount of 4,6-dihydroxypyrimidines continuously added and/or increasing the proportion of phosphoryl chloride in the reaction mixture and/or increasing the amount of recycled or recirculating completely reacted reaction mixture. However, such increases in the chemical yield tend to reduce the space-time yield.

EXAMPLES

Example 1 a) Starting phase:

To 2500 g of phosphoryl chloride, 28 g of 4,6-dihydroxypyrimidine (referred to below as DHP) were added at from 85° to 90° C. After this had gone completely into solution during the course of 25 minutes, 75 g of phosphorus trichloride were added, after which 35 g of chlorine gas at between 85° and 90° C. were introduced within 15 minutes. After gas evolution had ended, a further 28 g of DHP were added, and again, after this had gone into solution, 75 g of phosphorus trichloride and 35 g of chlorine were added to the reaction mixture as before. After 10 cycles, an amount was removed from the reaction mixture corresponding to the increase in weight (1,175 g).

After this had been removed, 250 g of phosphoryl chloride were added, so that the original starting amount of 2,500 g of phosphoryl chloride was restored, after which 5 further cycles were carried out and 825 g of reaction mixture were then removed.

This process was repeated two further times, whereupon 335 g of phosphoryl chloride were added, and, after 5 cycles, 910 g of reaction mixture were removed. After the addition of a further 400 g of phosphoryl chloride (5 further cycles) and the removal of 970 g of reaction mixture, the starting phase was concluded.

b) Continuity phase:

Subsequently, in every case, 425 g of phosphoryl chloride were added, 5 cycles were carried out, and, after this, a constant amount of 1,000 g of reaction mixture were removed. The reaction mixture removed was separated into its components by distillation. This first gave a small amount of phosphorus trichloride at 100 mbar, followed by the phosphoryl chloride at 100 mbar and a bottom temperature of max. 130° C., and finally, with the pressure reduced to 20 mbar and at a maximum bottom temperature of 175° C., the 4,6-dichloropyrimidine produced was removed. A distillation residue of 12% by weight of the 4,6-dichloropyrimidine obtained remained.

The distillation separation of the 1,000 g of reaction mixture from the continuity phase gave the following average figures:

20 g of phosphorus trichloride, 800 g of phosphoryl chloride, 160 g of 4,6-dichloropyrimidine, and 20 g of residue.

Based on the total of 140 g of DHP used, this corresponds to an average yield of 4,6-dichloropyrimidine of 85.9% of theory.

Example 2

The procedure was as in Example 1, but after carrying out the first 10 cycles and the removal of the excess produced at that stage, 80 g of phosphoryl chloride were added before each further cycle, and an amount of reaction mixture (200 g) corresponding to the increase in weight after each cycle was removed and worked up. The results are comparable to those of Example 1.

Example 3

The procedure was as in Example 1, but the 28 g of DHP were added to the reaction mixture not as solid but suspended in 75 g of phosphorus trichloride, and no phosphorus trichloride was added before the addition of the chlorine. The results were comparable to those of Example 1.

Example 4

In a 2001 slurrying kettle, 28 g/h of DHP were admixed with 75 kg/h of phosphorus trichloride, and the suspension obtained was pumped into the lower part of a multiple chamber reactor whose contents were maintained at 85° to 90° C. The multiple chamber reactor consisted of 8 chambers with a total volume of 2 m$^3$. At the same time, 80 kg/h of phosphoryl chloride and 3,160 kg/h of fully reacted reaction mixture were fed from a buffer tank through two other feeder pipes in the lower part of the multiple chamber reactor. 35 kg/h of gaseous chlorine are fed continuously through a feeder pipe in the middle part of the multichamber reactor.

The overflow from the multichamber reactor was collected in a buffer tank. From there, part of the reaction mixture was fed back into the multichamber reactor, and the rest (200 kg/h) was fed to a distillation work-up. There, excess phosphorus trichloride was removed in a first column, phosphoryl chloride was removed in a second column, and after addition of polyethylene glycol, the 4,6-dichloropyrimidine produced was recovered in a thin film evaporator at 100 mbar. 167 kg/h of 4,6-dichloropyrimidine were obtained, corresponding to a 4,6-dichloropyrimidine yield of 89.8% of theory.

Example 5 (for comparison)

460 g of phosphoryl chloride and 62 g of N,N-dimethylaniline were mixed, and 116 g of DHP (98% by weight) were metered into the mixture at 100° C. in the course of 5 hours by means of a screw feeder. The mixture was then stirred for 8 hours at 106° to 128° C. The reaction mixture was diluted with 300 g of chlorobenzene, and discharged onto 1.2 kg of ice. The organic phase was separated off, washed twice with 100 ml of water in each case, and then fractionally distilled. 85.7 g of 4,6-dichloropyrimidine (=58% of theory) were obtained.

What is claimed is:

1. A process for the preparation of 4,6-dichloropyrimidines by the reaction of 4,6-dihydroxypyrimidines with an excess of phosphoryl chloride, in which no base is added, after the reaction 0.7 to 1.3 mol of chlorine are added per equivalent of exchanged hydroxyl groups in the presence of phosphorus trichloride so that an excess of phosphorus trichloride with respect to chlorine is always present, and finally phosphorus trichloride and phosphoryl chloride are removed.

2. The process of claim 1, in which the 4,6-dihydroxypyrimidine is unsubstituted or substituted in position 2 and/or position 5 with $C_1$–$C_{10}$-alkyl and/or $C_6$–$C_{10}$-aryl groups or in position 5 with halogen.

3. The process of claim 1, in which for each mole of 4,6-dihydroxypyrimidine used, 2.5 to 12 mol of phosphoryl chloride are used.

4. The process of claim 1, in which the reaction of 4,6-dihydroxypyrimidine with phosphoryl chloride and the addition of phosphorus trichloride and chlorine are carried out at temperatures of 60° to 110° C.

5. The process of claim 1, which is carried out batchwise.

6. The process of claim 1, which is carried out semicontinuously.

7. The process of claim 1, which is carried out continuously.

8. The process of claim 1, in which 0.3 to 5% by weight of free phosphorus trichloride is always present in the reaction mixture.

9. The process of claim 1, in which the 4,6-dichloropyrimidine produced is separated off by distillation.

10. The process of claim 1, in which the 4,6-dichloropyrimidine produced is separated off by distillation with use of a driving liquid and/or a flow agent for the distillation residue.

* * * * *